(12) United States Patent
Aggerholm et al.

(10) Patent No.: US 9,011,481 B2
(45) Date of Patent: Apr. 21, 2015

(54) VASCULAR OCCLUSION DEVICE HAVING A JELLY FISH

(71) Applicants: Steen Aggerholm, Bjaelkerupvej (DK); Tue Thuren Bodewadt, Greve (DK)

(72) Inventors: Steen Aggerholm, Bjaelkerupvej (DK); Tue Thuren Bodewadt, Greve (DK)

(73) Assignee: Cook Medical Technologies LLC, Bloomington, IN (US)

( * ) Notice: Subject to any disclaimer, the term of this patent is extended or adjusted under 35 U.S.C. 154(b) by 23 days.

(21) Appl. No.: 13/800,109

(22) Filed: Mar. 13, 2013

(65) Prior Publication Data

US 2014/0188155 A1    Jul. 3, 2014

Related U.S. Application Data

(60) Provisional application No. 61/747,307, filed on Dec. 30, 2012.

(51) Int. Cl.
*A61M 29/00* (2006.01)
*A61B 17/12* (2006.01)

(52) U.S. Cl.
CPC ............................. *A61B 17/12022* (2013.01)

(58) Field of Classification Search
USPC .............. 606/135, 158, 157, 191–195, 200; 128/830–832, 839, 843; 623/1.24–1.26
See application file for complete search history.

(56) References Cited

U.S. PATENT DOCUMENTS

| | | | |
|---|---|---|---|
| 3,540,431 A | 11/1970 | Mebin-Uddin | |
| 4,577,631 A | 3/1986 | Kreamer | |
| 5,549,626 A | 8/1996 | Miller et al. | |
| 5,836,969 A | 11/1998 | Kim et al. | |
| 5,919,224 A * | 7/1999 | Thompson et al. | 606/200 |
| 5,989,281 A | 11/1999 | Barbut et al. | |
| 6,551,303 B1 | 4/2003 | Van Tassel et al. | |
| 6,652,555 B1 | 11/2003 | Van Tassel et al. | |
| 6,840,950 B2 | 1/2005 | Stanford et al. | |
| 7,326,225 B2 * | 2/2008 | Ferrera et al. | 606/200 |
| 7,992,565 B2 * | 8/2011 | McGuckin et al. | 128/831 |
| 2003/0057156 A1 | 3/2003 | Peterson et al. | |
| 2004/0167597 A1 | 8/2004 | Constantino et al. | |
| 2006/0009798 A1 | 1/2006 | Callister et al. | |
| 2007/0239194 A1* | 10/2007 | Tran et al. | 606/191 |
| 2008/0031919 A1* | 2/2008 | Henson et al. | 424/423 |
| 2009/0216263 A1* | 8/2009 | Tekulve | 606/200 |
| 2011/0152916 A1 | 6/2011 | Tripp et al. | |

\* cited by examiner

*Primary Examiner* — Todd Manahan
*Assistant Examiner* — Erich Herbermann
(74) *Attorney, Agent, or Firm* — Brinks, Gilson & Lione

(57) ABSTRACT

An occlusion device and a method of occluding a body vessel with the occlusion device are provided. The occlusion device has a sleeve that extends from a first end to a second end. The sleeve has an interior that extends to an opening at the first end. The occlusion device has tentacles that are attached to the first end and extend away from the sleeve. The tentacles reverse direction and extend into the interior to occlude the interior in response to fluid flowing toward the opening. A frame is attached to the first end of the sleeve.

22 Claims, 5 Drawing Sheets

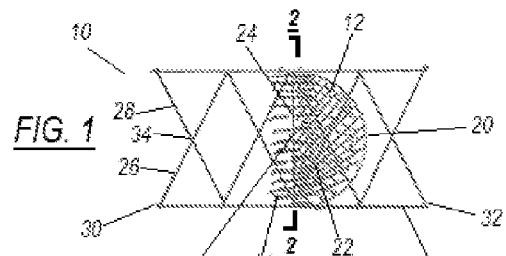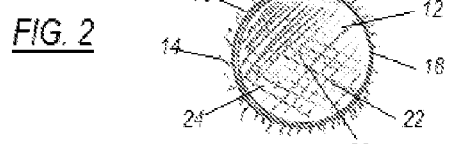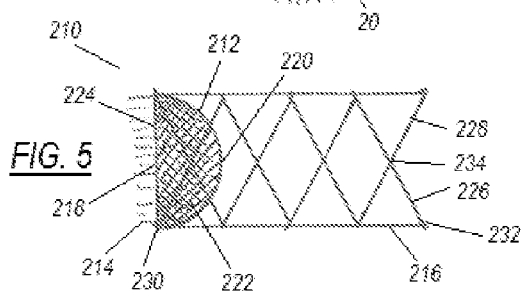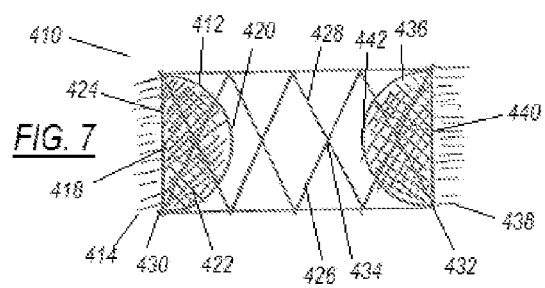

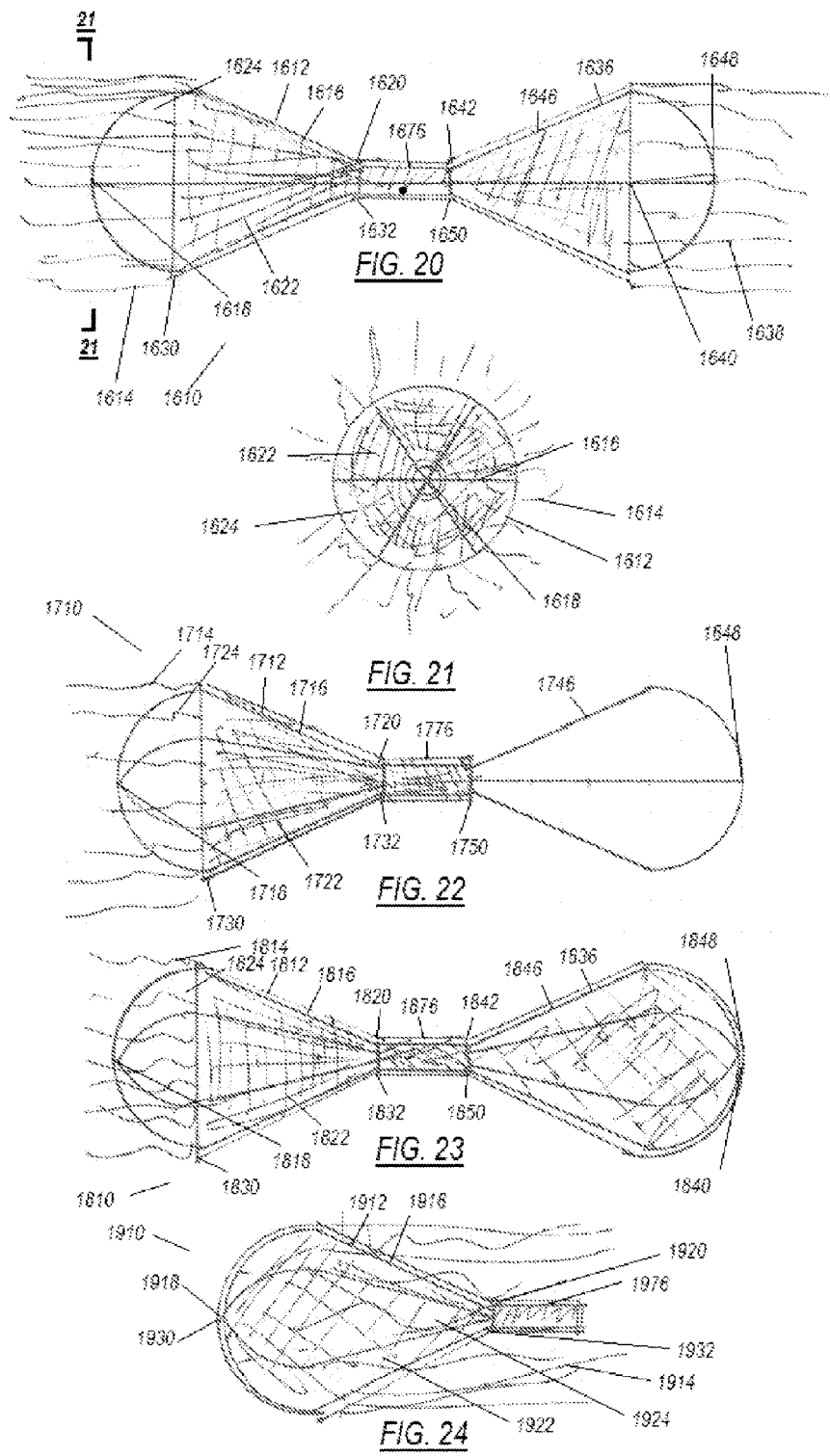

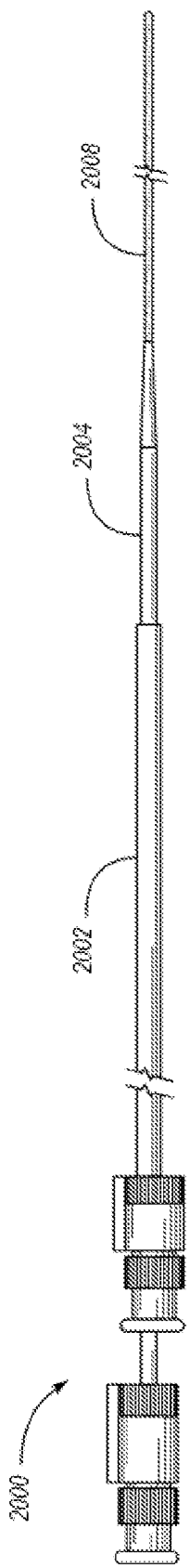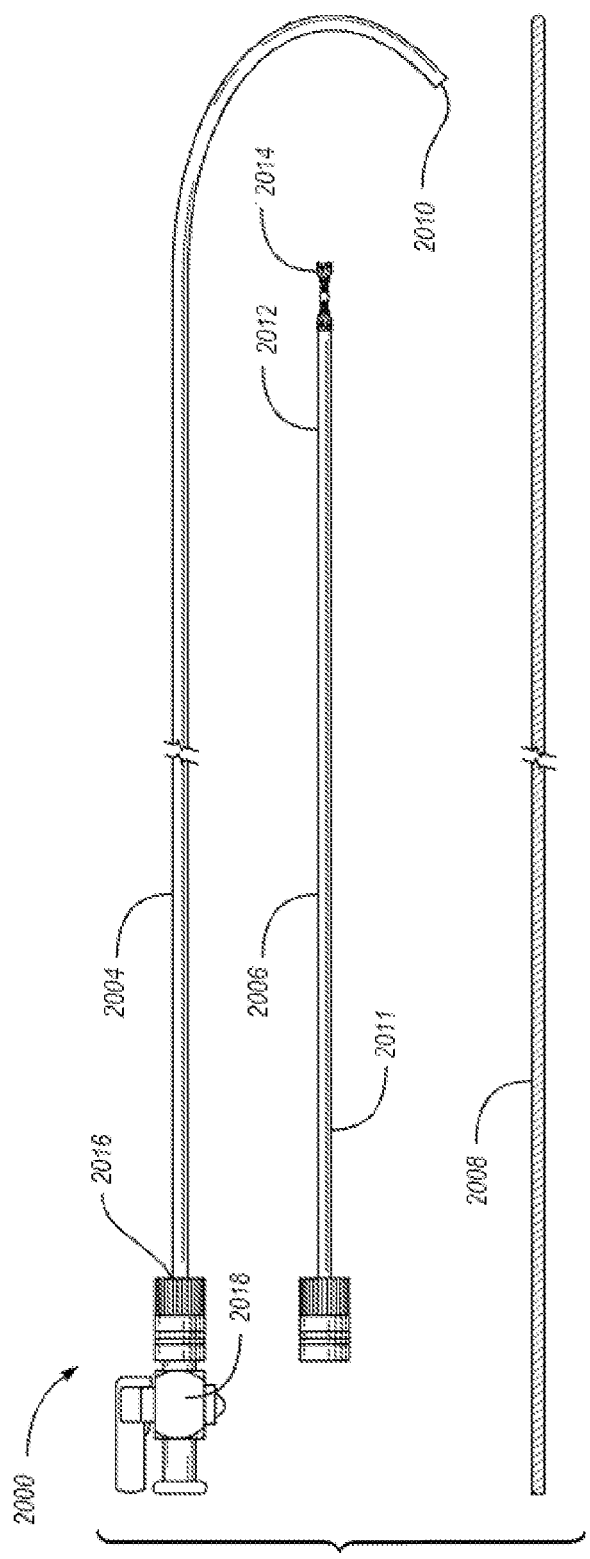
FIG. 25
FIG. 26

VASCULAR OCCLUSION DEVICE HAVING A JELLY FISH

CROSS REFERENCE TO RELATED APPLICATIONS

This application claims the benefit of U.S. Provisional Patent Application No. 61/747,307 filed Dec. 30, 2012, the content of which is hereby incorporated by reference in its entirety.

BACKGROUND

The present disclosure generally relates to medical devices. More specifically, the present disclosure relates to occlusion devices for occluding body vessels.

SUMMARY

In overcoming the drawbacks and other limitations of the related art, the present disclosure may provide an occlusion device for occluding a body vessel, and a method for occluding the body vessel with the occlusion device.

In some embodiments, the present disclosure may relate to an occlusion device for occluding a body vessel. The occlusion device may include a sleeve that extends from a first end to a second end. The sleeve may have an interior that extends to an opening at the first end. The occlusion device may include a plurality of tentacles attached to the first end and extending away from the sleeve. The plurality of tentacles may be configured to reverse direction and extend into the interior to occlude the interior in response to fluid flowing toward the opening. The occlusion device may include a frame attached to the first end of the sleeve.

In some embodiments, the present disclosure may relate to a method of occluding a body vessel with an occlusion device. The occlusion device may include a sleeve that extends from a first end to a second end. The sleeve may have an interior that extends to an opening at the first end. The occlusion device may include a plurality of tentacles attached to the first end and extending away from the sleeve. The occlusion device may include a frame attached to the first end of the sleeve. The method may include deploying the occlusion device in the body vessel to allow fluid to flow toward the opening. The method may include allowing the plurality of tentacles to reverse direction and extend into the interior to occlude the interior in response to the fluid flowing toward the opening.

In some embodiments, the present disclosure may relate to a delivery assembly for placing and retrieving an occlusion device for occluding an opening in a body tissue. The assembly may include an outer sheath having a tubular body extending from a proximal part to a distal part. The tubular body may include a sheath lumen extending therethrough. The assembly may include an inner member extending from a proximal portion to a distal portion. The inner member may be disposed within the sheath lumen and configured for longitudinal movement relative to the outer sheath. The occlusion device may be coaxially disposed within the sheath lumen and removably coupled to the distal portion of the inner member and deployable through the distal part of the outer sheath by means of the relative longitudinal movement of the inner member. The occlusion device may include a sleeve that extends from a first end to a second end. The sleeve may have an interior that extends to an opening at the first end. The occlusion device may include a plurality of tentacles attached to the first end and extending away from the sleeve. The plurality of tentacles may be configured to reverse direction and extend into the interior to occlude the interior in response to fluid flowing toward the opening. The occlusion device may include a frame attached to the first end of the sleeve.

Further features and advantages of the present disclosure will become apparent from consideration of the following description and the appended claims when taken in connection with the accompanying drawings. It should be understood that the description and specific examples are intended for purposes of illustration only and are not intended to limit the scope of the present disclosure.

BRIEF DESCRIPTION OF THE DRAWINGS

FIG. 1 is a side view of an occlusion device in accordance with some embodiments of the present disclosure;

FIG. 2 is an end view of the occlusion device of FIG. 1 in accordance with some embodiments of the present disclosure;

FIG. 3 is a side view of an occlusion device in accordance with some embodiments of the present disclosure;

FIG. 4 is an end view of the occlusion device of FIG. 3 in accordance with some embodiments of the present disclosure;

FIG. 5 is a side view of an occlusion device in accordance with some embodiments of the present disclosure;

FIG. 6 is a side view of an occlusion device in accordance with some embodiments of the present disclosure;

FIG. 7 is a side view of an occlusion device in accordance with some embodiments of the present disclosure;

FIG. 8 is a side view of an occlusion device in accordance with some embodiments of the present disclosure;

FIG. 9 is a side view of an occlusion device in accordance with some embodiments of the present disclosure;

FIG. 10 is a side view of an occlusion device in accordance with some embodiments of the present disclosure;

FIG. 20 is a side view of an occlusion device in accordance with some embodiments of the present disclosure;

FIG. 21 is an end view of the occlusion devices of FIG. 20 in accordance with some embodiments of the present disclosure;

FIG. 22 is a side view of an occlusion device in accordance with some embodiments of the present disclosure;

FIG. 23 is a side view of an occlusion device in accordance with some embodiments of the present disclosure;

FIG. 24 is a side view of an occlusion device in accordance with some embodiments of the present disclosure;

FIG. 25 a side view of a delivery and retrieval assembly for use with an occlusion device in accordance with some embodiments of the present disclosure;

FIG. 26 is an exploded view of the delivery and retrieval assembly of FIG. 25 in accordance with some embodiments of the present disclosure.

Figure 11:
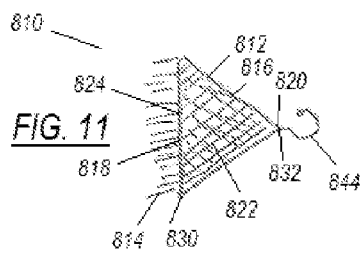
FIG. 11 is a side view of an occlusion device in accordance with some embodiments of the present disclosure.

The drawings described herein are for illustration purposes only and are not intended to limit the scope of the present disclosure in any way.

DETAILED DESCRIPTION

The present disclosure generally provides an occlusion device for occluding a body vessel, and a method for occluding a body vessel with the occlusion device. Embodiments of the present disclosure may provide a more effective occlusion body a vessel, may be more cost-effective, and may reduce procedure time relative to placement of plugs or multiple coils. The occlusion device may be used, for example, by interventional radiologists, cardiologists, and vascular surgeons for arterial and venous embolization in the peripheral vasculature.

The terms "substantially" or "about" used herein with reference to a quantity includes variations in the recited quantity that are equivalent to the quantity recited, such as an amount that is equivalent to the quantity recited for an intended purpose or function. The term "woven fibers" used herein is defined as fibers interlaced together so as to overlap each other. The term "braided fibers" used herein is defined as three or more fibers interweaved in an overlapping pattern.

FIGS. 1 and 2 illustrate an occlusion device 10 in accordance with some embodiments of the present disclosure. The occlusion device 10 may include a sleeve 12, tentacles 14, and a frame 16. As shown, the occlusion device 10 is in a radially expanded configuration intended for when the occlusion device 10 is deployed. However, the occlusion device 10 may also be configured to be in a radially collapsed configuration during delivery and retrieval of the occlusion device 10.

The sleeve 12 may extend from a first end 18 to a second end 20 to define a longitudinal axis. The second end 20 may be rounded such that the sleeve 12 may be shaped as a half-sphere. The sleeve 12 may taper (e.g. continuously taper) in diameter from the first end 18 to the second 20. The sleeve 12 may have an interior 22 that extends to an opening 24 at the first end 18. The interior 22 may be hollow. The opening 24 may have a circular shape, as shown in FIG. 2. The sleeve 12 may be made of any suitable material such as one or more of molded fibers, woven fibers, braided fibers, extracellular matrix (ECM), and/or non-woven textiles. The sleeve 12 may be made of a flexible material such that it can be radially expanded and collapsed. In some embodiments, the sleeve 12 may be made of very thin, tight, woven fibers, for example Dyneema 10dtex fibers.

The tentacles 14 may be attached to the first end 18 to create a circumferential attachment pattern at attachment points around the circular opening 24. The number, spacing, and/or length of the tentacles 14 may be selected for sufficient occlusion of a body vessel. The tentacles 14 may each be long, thin fibers. The tentacles 14 may extend away (e.g., longitudinally away) from the sleeve 14. The tentacles 14 may extend longitudinally away and parallel to the longitudinal axis, or may instead extend longitudinally away from the sleeve 14 and also flare radially outwardly from the attachment points on the first end 18. The tentacles 14 may be configured to reverse direction and extend into (e.g. be immediately pushed into) the interior 22 to occlude (e.g. instantaneously occlude) the interior 22. The tentacles 14 may also be configured to extend radially inwardly in response to fluid flow (e.g. in embodiments when the tentacles 14 flare radially away prior to contact with fluid flow). The tentacles 14 may thus be caused to become crowded together (e.g. bunched together) to form an occlusive mass in the interior 22. The occlusion can be complete or partial, depending on the properties of the tentacles 14, e.g. the number, size, and spacing of the tentacles 14. In embodiments where occlusion is partial, the number, size, and spacing of the tentacles 14 can be selected to occlude only certain objects or fluids, e.g. fluids of a particular density, fluids exceeding a particular density, or objects exceeding a certain mass or density. If the occlusion device 10 is in a lumen of a guide wire the tentacles 14 may occlude the lumen of the guide wire and other minor leaks in response to fluid (e.g. blood) flowing toward the opening 24. The tentacles 14 may be made of one of the materials that the sleeve 12 may be made of. Thus, the tentacles 14 may be made of the same or a different material than the sleeve 14. In some embodiments, both the sleeve 12 and tentacles 14 may be made of Dyneema 10dtex fibers. In embodiments where both the sleeve 12 and tentacles 14 are fibers, the sleeve 12 and tentacles 14 may be integral. For example, each of the fibers from which each tentacle 14 may be made may also be among the fibers from which the sleeve 14 may be made. In some embodiments, the fibers from which the tentacles 14 may be made may be different from the fibers from which the sleeve 12 may be made. For example, each tentacle 14 (and e.g. its fibers) may be tied, sewn (e.g. with sutures), glued, molded, or soldered to the sleeve 14 and/or the frame 16. The sleeve 12 and tentacles 14 may together have a "jelly fish" shaped configuration.

The frame 16 may have a tubular shape that may have a constant or substantially constant diameter along its longitudinal length from its first end 30 to its second end 32. For example, the frame 16 may be a scaffold formed from a plurality of interconnected and articulated members 26. The articulated members may be arranged to form a self-expanding ring shaped structure 28. A plurality of the ring structures 28 may be, for example, coaxially aligned from the first end 30 to the second end 32 of the frame 16 along the longitudinal axis. Each of the ring structures 28 are attached to at least one adjacent ring structure 28. The ring structures 28 may be attached together at joints 34. In other examples, the ring structures 28 may be attached together by a plurality of longitudinal members. In yet another example, the articulated members 26 and joints 34 may be configured to form a sinusoidal pattern. It should be understood that the scaffold may include any of a variety of self-expanding devices such as, for example, stents. Some examples of self-expanding stents include, but are not limited to, those disclosed in U.S. Pat. Nos. 4,580,568; 5,035,706; 5,507,767; 6,042,606; and U.S. Pub. No. 2009/0062839, all of which are hereby incorporated by reference herein in their entireties.

The frame 16 may include hooks attached to and extending from the outer surface of the frame 16 to prevent migration of the occlusion device 10. The hooks may also be attached to the sleeve 12 to secure the sleeve 12 to the frame 16. The frame 16 may also include a retrieval member (e.g. a hook or loop) to allow a grasping member (e.g. a snare) to grasp the occlusion device 10 for retrieval. The sleeve 12 may be attached to and located in the interior of the frame 16. As shown in FIG. 1, the entire circumference of the circular first end 18 of the sleeve 12 may be attached along and to the entire circumference of a middle portion of the tubular frame 16.

The frame 16 (e.g. its wires) may be made of any suitable material such as a superelastic material, high density polymeric material, steel, stainless steel wire, cobalt-chromium-nickel-molybdenum-iron alloy, cobalt-chrome, copper-zinc-aluminum, copper-aluminum-nickel alloy, biodegradable material, collagen, and/or biomaterials, The frame 16 may be cut (e.g. laser cut) or made of tread. In some embodiments, the frame 16 may be made of any other suitable material that will result in a self-coiling device, such as shape memory alloys. Shape memory alloys have the desirable property of becoming rigid, that is, returning to a remembered state, when heated above a transition temperature. A shape memory alloy suitable for the present invention is Ni—Ti available under the more commonly known name Nitinol. When this material is heated above the transition temperature, the material undergoes a phase transformation from martensite to austenite, such that the material returns to its remembered state. The transition temperature is dependent on the relative proportions of the alloying elements Ni and Ti and the optional inclusion of alloying additives.

In some embodiments, the frame 16 may be made from Nitinol with a transition temperature that is below normal body temperature of humans (i.e., below 98.6° F.). Thus, when the occlusion device 10 is deployed in a body vessel and exposed to normal body temperature, the alloy in the occlusion device 100 transforms to austenite, such that the device returns from a radially collapsed state to its remembered state, which may be a radially expanded state.

In some embodiments, the frame 16 may not self-expand or self-collapse based on temperature changes. The frame 16 may have elastic or superelastic properties. Thus, radial expansion and radial collapse of the frame 16 may be accomplished by applying an external force to the frame. For example, the frame 16 may be biased to a radially expanded state, and may enter the radially collapsed state upon application of an inward radial force. Ending the external inward radial force and applying no further external forces may cause the frame 16 to return to the biased radially expanded state.

The radial expansion or radial collapse of the frame 16 may also cause the occlusion device 10, including the sleeve 12 (which may be flexible) as a whole to radially expand or radially collapse. Thus, the expansion or contraction of the frame 16 may control the expansion or contraction of the sleeve 12.

FIGS. 3 and 4 illustrate an occlusion device 110 in accordance with some embodiments of the present disclosure. The occlusion device 110 may include a sleeve 112, tentacles 114, and a frame 116. The sleeve 112 may extend from a first end 118 to a second end 120. The sleeve 112 may have an interior 122 that extends to an opening 124 at the first end 118. The frame 116 may be a scaffold formed from articulated members 126 which may form ring structures 128 that are coaxially aligned from a first end 130 to a second end 132 of the frame 116. The ring structures 128 may be attached together at joints 134. The occlusion device 110 may be similar in all respects to the occlusion device 10 of FIGS. 1 and 2, except that the sleeve 112 may have a conical shape. Thus, the second end 120 may be a sharp or rounded end. The sleeve 112 may taper (e.g. continuously taper) in diameter from the first end 118 to the second 120.

FIG. 5 illustrates an occlusion device 210 in accordance with some embodiments of the present disclosure. The occlusion device 210 may include a sleeve 212, tentacles 214, and a frame 216. The sleeve 212 may extend from a first end 218 to a second end 220. The sleeve 212 may have an interior 222 that extends to an opening 224 at the first end 218. The frame 216 may be a scaffold formed from articulated members 226 which may form ring structures 228 that are coaxially aligned from a first end 230 to a second end 232 of the frame 216. The ring structures 228 may be attached together at joints 234. The occlusion device 210 may be similar in all respects to the occlusion device 10 of FIGS. 1 and 2, except that the entire circumference of the circular first end 218 of the sleeve 212 may be attached along and to the entire circumference of the first end 230, rather than a middle portion, of the tubular frame 216. In these embodiments, a balloon may be used to expand to frame 216 during deployment by expanding the balloon in the empty part of the interior of the frame 216.

FIG. 6 illustrates an occlusion device 310 in accordance with some embodiments of the present disclosure. The occlusion device 310 may include a sleeve 312, tentacles 314, and a frame 316. The sleeve 312 may extend from a first end 318 to a second end 320. The sleeve 312 may have an interior 322 that extends to an opening 324 at the first end 318. The frame 316 may be a scaffold formed from articulated members 326 which may form ring structures 328 that are coaxially aligned from a first end 330 to a second end 332 of the frame 316. The ring structures 328 may be attached together at joints 334. The occlusion device 310 may be similar in all respects to the occlusion device 110 of FIGS. 3 and 4, except that the entire circumference of the circular first end 318 of the sleeve 312 may be attached along and to the entire circumference of the first end 330, rather than a middle portion, of the tubular frame 316. In these embodiments, a balloon may be used to expand to frame 216 during deployment by expanding the balloon in the empty part of the interior of the frame 216.

FIG. 7 illustrates an occlusion device 410 in accordance with some embodiments of the present disclosure. The occlusion device 410 may include a sleeve 412, tentacles 414, and a frame 416. The sleeve 412 may extend from a first end 418 to a second end 420. The sleeve 412 may have an interior 422 that extends to an opening 424 at the first end 418. The frame 416 may be a scaffold formed from articulated members 426 which may form ring structures 428 that are coaxially aligned from a first end 430 to a second end 432 of the frame 416. The ring structures 428 may be attached together at joints 434. The occlusion device 410 may be similar in all respects to the occlusion device 210 of FIG. 5, except that the occlusion device 210 may include a second sleeve 436 and second tentacles 438 which may be similar to the sleeve 412 and tentacles 414. The second sleeve 436 may extend from first end 440 to second end 442. The second sleeve 436 and second tentacles 438 may be reversed in direction relative to the sleeve 412 and tentacles 414 such that the second ends 420 and 442 face each other, and the first ends 418 and 440 each face outwardly. The entire circumference of the circular first end 440 of the second sleeve 436 may be attached along and to the entire circumference of the second end 432 of the tubular frame 416.

FIG. 8 illustrates an occlusion device 510 in accordance with some embodiments of the present disclosure. The occlusion device 510 may include a sleeve 512, tentacles 514, and a frame 516. The sleeve 512 may extend from a first end 518 to a second end 520. The sleeve 512 may have an interior 522 that extends to an opening 524 at the first end 518. The frame 516 may be a scaffold formed from articulated members 526 which may form ring structures 528 that are coaxially aligned from a first end 530 to a second end 532 of the frame 516. The ring structures 528 may be attached together at joints 534. The occlusion device 510 may be similar in all respects to the occlusion device 310 of FIG. 6, except that the occlusion device 510 may include a second sleeve 536 and second tentacles 538 which may be similar to the sleeve 512 and tentacles 514. The second sleeve 536 may extend from first end 540 to second end 542. The second sleeve 536 and second tentacles 538 may be reversed in direction relative to the sleeve 512 and tentacles 514 such that the second ends 520 and 542 face each other and are attached to each other (e.g. tied, sewen, sutured, molded to each other), and the first ends 518 and 540 each face outwardly. The entire circumference of the circular first end 540 of the second sleeve 536 may be attached along and to the entire circumference of the second end 532 of the tubular frame 516.

FIG. 9 illustrates an occlusion device 610 in accordance with some embodiments of the present disclosure. The occlusion device 610 may include a sleeve 612, tentacles 614, a frame 616, a second sleeve 636, and second tentacles 638. The sleeve 612 may extend from a first end 618 to a second end 620. The sleeve 612 may have an interior 622 that extends to an opening 624 at the first end 618. The frame 616 may be a scaffold formed from articulated members 626 which may form ring structures 628 that are coaxially aligned from a first end 630 to a second end 632 of the frame 616. The ring structures 628 may be attached together at joints 634. The second sleeve 636 may extend from first end 640 to second end 642. The occlusion device 610 may be similar in all respects to the occlusion device 410 of FIG. 7, except that the sleeves 612 and 636 may be tilted at an angle with respect to the longitudinal axis to facilitate easier collapse of the occlusion device 610 when loaded in a delivery system. Thus, part of the circular first end 618 of the sleeve 612 may be attached to the first end 630 of the frame 616, and another part of the circular first end 618 may be attached to the middle portion of the frame 616. Additionally, part of the circular first end 640 of the second sleeve 612 may be attached to the second end 632 of the frame 616, and another part of the circular first end 640 may be attached to the middle portion of the frame 616.

FIG. 10 illustrates an occlusion device 710 in accordance with some embodiments of the present disclosure. The occlusion device 710 may include a sleeve 712, tentacles 714, a frame 716, a second sleeve 736, and second tentacles 738. The sleeve 712 may extend from a first end 718 to a second end 720. The sleeve 712 may have an interior 722 that extends to an opening 724 at the first end 718. The frame 716 may be a scaffold formed from articulated members 726 which may form ring structures 728 that are coaxially aligned from a first end 730 to a second end 732 of the frame 716. The ring structures 728 may be attached together at joints 734. The second sleeve 736 may extend from first end 740 to second end 742. The occlusion device 710 may be similar in all respects to the occlusion device 510 of FIG. 8, except that the sleeves 712 and 736 may be tilted at an angle with respect to the longitudinal axis to facilitate easier collapse of the occlusion device 710 when loaded in a delivery system. Thus, part of the circular first end 718 of the sleeve 712 may be attached to the first end 730 of the frame 716, and another part of the circular first end 718 may be attached to the middle portion of the frame 716. Additionally, part of the circular first end 740 of the second sleeve 712 may be attached to the second end 732 of the frame 716, and another part of the circular first end 740 may be attached to the middle portion of the frame 716.

FIG. 11 illustrates an occlusion device 810 in accordance with some embodiments of the present disclosure. The occlusion device 810 may include a sleeve 812, tentacles 814, and a frame 816. The sleeve 812 may extend from a first end 818 to a second end 820. The sleeve 812 may have an interior 822 that extends to an opening 824 at the first end 818. The sleeve 812 and tentacles 814 may be similar in all respects to the sleeve 12 and tentacles 14 of FIG. 1. However, the frame 816 may instead have a conical shape that conforms to the shape of the sleeve 812. The frame 816 may extend between and taper (e.g. continuously taper) in diameter from a first end 830 to a second end 832. The second end 830 may be a sharp or rounded end. The frame 816 may be made of wires, for example woven and/or braided wires. Some examples of frames that may be used include, but are not limited to, those disclosed in U.S. Pat. No. 5,133,733 (e.g. the Tulip filter) and U.S. Pat. No. 7,625,390 (e.g. the Celect filter), each of which are hereby incorporated by reference herein in their entireties. The entire circumference of the circular first end 818 of the sleeve 812 may be attached along and to the entire circumference of the circular first end 830 of the frame 816. Additionally, the body of the sleeve 812 between the first end 818 and second end 820 may be attached to the body of the frame 816 between the first end 830 and second end 832. The sleeve 812 may be attached to the exterior of the frame 816 or to the interior of the frame 816. The frame 816 may include a retrieval member 844 (e.g. a hook or loop) attached to the second end 832 to allow a grasping member (e.g. a snare) to grasp the occlusion device 810 for retrieval. As shown in FIG. 1, the entire circumference of the circular first end 818 of the sleeve 812 may be attached along and to the entire circumference of a middle portion of the tubular frame 816. The frame 812 may otherwise have similar properties as described with respect to frame 12 of FIG. 1.

Figure 12:
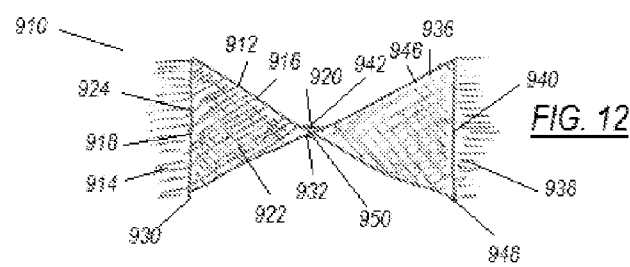
FIG. 12 is a side view of an occlusion device in accordance with some embodiments of the present disclosure.

FIG. 12 illustrates an occlusion device 910 in accordance with some embodiments of the present disclosure. The occlusion device 910 may include a sleeve 912, tentacles 914, and a frame 916. The sleeve 912 may extend from a first end 918 to a second end 920. The sleeve 912 may have an interior 922 that extends to an opening 924 at the first end 918. The frame 916 may extend between a first end 930 and a second end 932. The occlusion device 910 may be similar in all respects to the occlusion device 810 of FIG. 11, except that it may not have the retrieval member 844, and that it may have a second sleeve 936 and second tentacles 938 which may be similar to the sleeve 912 and tentacles 914. The second sleeve 936 may extend from first end 940 to second end 942. The second sleeve 936 and second tentacles 938 may be reversed in direction relative to the sleeve 912 and tentacles 914 such that the second ends 920 and 942 face each other (and depending on the embodiments, may or may not be attached to each other), and the first ends 918 and 940 each face outwardly. The occlusion device 910 may also include a second frame 946 which may be similar to the frame 916. The second frame 946 may extend between a first end 948 and a second end 950. The second ends 932 and 950 may be attached to each other, either directly or through a hub that may be made of one or more materials that the frames 916 and 946 are made of. The second sleeve 936 and second frame 946 may be attached to each other in a similar way as the sleeve 912 and frame 916. Additionally, having two frames 916 and 946 may aid in stability and placement of the occlusion device 910 such that the occlusion device 910 may not tilt in a body vessel.

Figure 13:
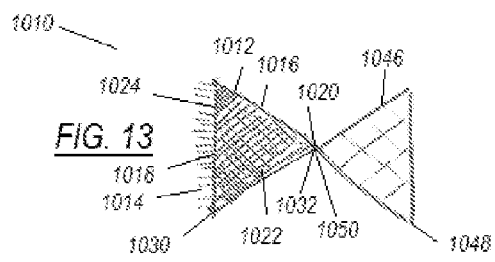
FIG. 13 is a side view of an occlusion device in accordance with some embodiments of the present disclosure.

FIG. 13 illustrates an occlusion device 1010 in accordance with some embodiments of the present disclosure. The occlusion device 1010 may include a sleeve 1012, tentacles 1014, frame 1016, and second frame 1046. The sleeve 1012 may extend from a first end 1018 to a second end 1020. The sleeve 1012 may have an interior 1022 that extends to an opening 1024 at the first end 1018. The frame 1016 may extend between a first end 1030 and a second end 1032. The second frame 1046 may extend between a first end 1048 and a second end 1050. The occlusion device 1010 may be similar in all respects to the occlusion device 910 of FIG. 12, except that it may lack the second sleeve 936.

Figures 14, 15:
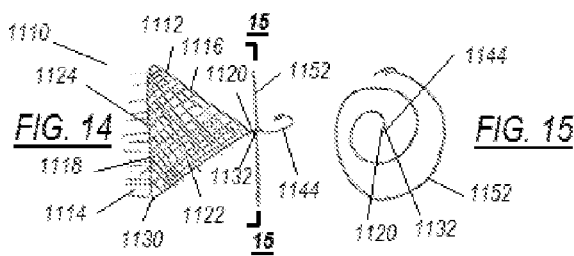
FIG. 14 is a side view of an occlusion device in accordance with some embodiments of the present disclosure.
FIG. 15 is an end view of the occlusion device of FIG. 14 in accordance with some embodiments of the present disclosure.

FIGS. 14 and 15 illustrate an occlusion device 1110 in accordance with some embodiments of the present disclosure. The occlusion device 1110 may include a sleeve 1112, tentacles 1114, and frame 1116. The sleeve 1112 may extend from a first end 1118 to a second end 1120. The sleeve 1112 may have an interior 1122 that extends to an opening 1124 at the first end 1118. The frame 1116 may extend between a first end 1130 and a second end 1132. The frame 1116 may include a retrieval member 1144. The occlusion device 1110 may be similar in all respects to the occlusion device 1010 of FIG. 11, except that it may additionally include a stabilizing member 1152, which may be a wire that spirals outwardly along a geometric plane from a first end 1154 and a second end 1156. The first end 1154 may be attached to the second end 1132, second end 1120, and/or the retrieval member 1144. Additionally, the stabilizing member 1152 may aid in stability and placement of the occlusion device 1110 such that the occlusion device 1110 may not tilt in a body vessel.

Figures 16, 17:
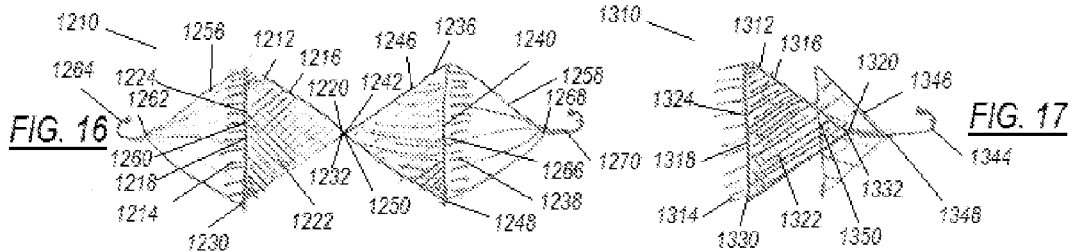
FIG. 16 is a side view of an occlusion device in accordance with some embodiments of the present disclosure.
FIG. 17 is a side view of an occlusion device in accordance with some embodiments of the present disclosure.

FIG. 16 illustrates an occlusion device 1210 in accordance with some embodiments of the present disclosure. The occlusion device 1210 may include a sleeve 1212, tentacles 1214, frame 1216, second sleeve 1236, and second frame 1246. The sleeve 1212 may extend from a first end 1218 to a second end 1220. The sleeve 1212 may have an interior 1222 that extends to an opening 1224 at the first end 1218. The frame 1216 may extend between a first end 1230 and a second end 1232. The second sleeve 1236 may extend from first end 1240 to second end 1242. The second frame 1246 may extend between a first end 1248 and a second end 1250. The occlusion device 1210 may be similar in all respects to the occlusion device 910 of FIG. 12, except that it may additionally include third frame 1256 and fourth frame 1258. The third frame 1256 may extend between and taper (e.g. continuously taper) in diameter from a circular first end 1260 to a second end 1262. The circular first end 1260 of the third frame 1256 may be attached at circumferential attachment points to the circular first end 1230 of the frame 1216. The second end 1262 may be a sharp end or a rounded end. The third frame 1256 may include a retrieval member 1264 (e.g. a hook or loop) attached to the second end 1262 to allow a grasping member (e.g. a snare) to grasp the occlusion device 1210 for retrieval. The fourth frame 1258 may extend between and taper (e.g. continuously taper) in diameter from a circular first end 1266 to a second end 1268. The circular first end 1266 of the fourth frame 1258 may be attached at circumferential attachment points to the circular first end 1248 of the second frame 1246. The second end 1268 may be a sharp end or a rounded end. The fourth frame 1258 may include a retrieval member 1270 (e.g. a hook or loop) attached to the second end 1268 to allow a grasping member (e.g. a snare) to grasp the occlusion device 1210 for retrieval. The third and fourth frames 1256 and 1258 may be made of wires, for example woven and/or braided wires. In some embodiments, the third and fourth frames 1256 and 1258 may each be made of a set of longitudinal wires which extend respectively from first ends 1260 and 1266 to and are attached to each other at the respective second ends 1262 and 1268 to form a conical shape. The third and fourth frames 1256 and 1258 may be made of one or more of the materials that the first and second frames 1216 and 1246 are made of, and may have the same expansion and collapse properties as the first and second frames 1216 and 1246.

FIG. 17 illustrates an occlusion device 1310 in accordance with some embodiments of the present disclosure. The occlusion device 1310 may include a sleeve 1312, tentacles 1314, and a frame 1316. The sleeve 1312 may extend from a first end 1318 to a second end 1320. The sleeve 1312 may have an interior 1322 that extends to an opening 1324 at the first end 1318. The frame 1316 may extend between a first end 1330 and a second end 1332. The frame 1316 may include a retrieval member 1344. The occlusion device 1310 may be similar in all respects to the occlusion device 810 of FIG. 11, except that it may additionally include a second frame 1346 which may be similar to the frame 1316. The second frame 1346 may extend between a first end 1348 and a second end 1350. The second end 1350 may be attached to a middle portion of the retrieval member 1344, which is shown as a hook in FIG. 17. Additionally, the second frame 1346 may aid in stability and placement of the occlusion device 1310 such that the occlusion device 1310 may not tilt in a body vessel.

Figures 18, 19:
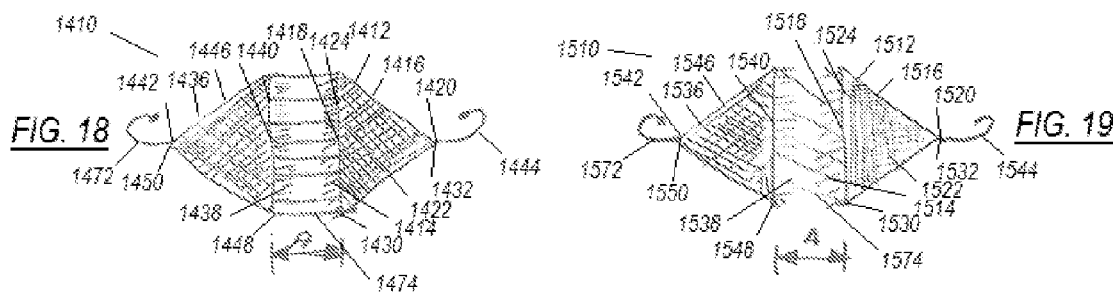
FIG. 18 is a side view of an occlusion device in accordance with some embodiments of the present disclosure.
FIG. 19 is a side view of an occlusion device in accordance with some embodiments of the present disclosure.

FIG. 18 illustrates an occlusion device 1410 in accordance with some embodiments of the present disclosure. The occlusion device 1410 may include a sleeve 1412, tentacles 1414, and a frame 1416. The sleeve 1412 may extend from a first end 1418 to a second end 1420. The sleeve 1412 may have an interior 1422 that extends to an opening 1424 at the first end 1418. The frame 1416 may extend between a first end 1430 and a second end 1432. The frame 1416 may include a retrieval member 1444. The occlusion device 1410 may be similar in all respects to the occlusion device 810 of FIG. 11, except that it may have a second sleeve 1436, second tentacles 1438, and second retrieval member 1472 which may be similar to the sleeve 1412, tentacles 1414, and retrieval member 1444. The occlusion device 1410 may also additionally include longitudinal attachment members 1474. The second sleeve 1436 may extend from first end 1440 to second end 1442. The second sleeve 1436 and second tentacles 1438 may be reversed in direction relative to the sleeve 1412 and tentacles 1414 such that the first ends 1418 and 1440 face each other (and in some embodiments, may or may not be attached to each other), and the second ends 1420 and 1442 each face outwardly. The occlusion device 1410 may also include a second frame 1446 which may be similar to the frame 1416. The second frame 1446 may extend between a first end 1448 and a second end 1450. The second sleeve 1436 and second frame 1446 may be attached to each other in a similar way as the sleeve 1412 and frame 1416. The second retrieval member 1472 may be attached to the second end 1450 of the second frame 1446. The longitudinal attachment members 1474 may be wires, and may made of one or more of the materials that the first and second frames 1416 and 1446 may be made of. The longitudinal attachment members 1474 may be circumferentially spaced to form a circular pattern, so as to attach the circular first ends 1430 and 1448 of the first and second frames 1416 and 1446. The first ends 1430 and 1448 may be spaced apart by distance "A". The longitudinal attachment members 1474 may be parallel or substantially parallel to the longitudinal axis. In some embodiments, fluid may be able to flow through the openings between the longitudinal attachment members 1474.

FIG. 19 illustrates an occlusion device 1510 in accordance with some embodiments of the present disclosure. The occlusion device 1510 may include a sleeve 1512, tentacles 1514, a frame 1616, second sleeve 1536, second tentacles 1538, and second frame 1546. The sleeve 1512 may extend from a first end 1518 to a second end 1520. The sleeve 1512 may have an interior 1522 that extends to an opening 1524 at the first end 1518. The frame 1516 may extend between a first end 1530 and a second end 1532. The second sleeve 1536 may extend from first end 1540 to second end 1542. The second frame 1546 may extend between a first end 1448 and a second end 1450. The frame 1516 may include a retrieval member 1544, and the second frame 1546 may include a second retrieval member 1572. The occlusion device 1510 may also include longitudinal attachment members 1574. The occlusion device 1510 may be similar in all respects to the occlusion device 1410 of FIG. 18, except that the longitudinal attachment members 1574 may be tilted at an angle relative to the longitudinal axis, but may remain parallel or substantially parallel to each other.

FIGS. 20 and 21 illustrate an occlusion device 1610 in accordance with some embodiments of the present disclosure. The occlusion device 1610 may include a sleeve 1612, tentacles 1614, frame 1616, second sleeve 1636, second tentacles 1638, and second frame 1646. The sleeve 1612 may extend from a first end 1618 to a second end 1620. The sleeve 1612 may have an interior 1622 that extends to an opening 1624 at the first end 1618. The frame 1616 may extend between a first end 1630 and a second end 1632. The second sleeve 1636 may extend from first end 1640 to second end 1642. The second frame 1646 may extend between a first end 1648 and a second end 1650. The occlusion device 1610 may be similar in all respects to the occlusion device 910 of FIG. 12, except that the two frames 1616 and 1636 may instead be made of longitudinal members (e.g. wires) extending in opposing directions from a tubular hub 1676 attached to the respective second ends 1632 and 1650. The hub 1676 may be made of one or more of the materials discussed earlier that the frames 1616 and 1636 may be made of. The longitudinal members may extend both longitudinally and radially outwardly from the hub 1676 until they reach inflection points and may continue to extend longitudinally away but curve radially inwardly to meet at the respective rounded first ends 1618 and 1648. The rounded first ends 1618 and 1648 may be grasped by a grasping member (e.g. a snare) to grasp the occlusion device 1610 for retrieval. The rounded first ends may be porous (thereby having the opening 1624) to allow fluid to flow through. The first ends 1616 and 1640 of the sleeves 1612 and 1636 may be attached to the longitudinal members at the inflection points (or substantially at the inflection points). A middle sleeve portion 1678 may also be attached to the interior or exterior of the hub 1676, and may be attached to the second ends 1620 and 1642 of the sleeves 1612 and 1636.

FIG. 22 illustrates an occlusion device 1710 in accordance with some embodiments of the present disclosure. The occlusion device 1710 may include a sleeve 1712, tentacles 1714, frame 1716, second frame 1746, tubular hub 1776, and middle sleeve portion 1778. The sleeve 1712 may extend from a first end 1718 to a second end 1720. The sleeve 1712 may have an interior 1722 that extends to an opening 1724 at the first end 1718. The frame 1716 may extend between a first end 1730 and a second end 1732. The second frame 1746 may extend between a first end 1748 and a second end 1750. The occlusion device 1710 may be similar in all respects to the occlusion device 1610 of FIG. 21, except that the occlusion device 1710 may lack the second sleeve 1636 and second tentacles 1638.

FIG. 23 illustrates an occlusion device 1810 in accordance with some embodiments of the present disclosure. The occlusion device 1810 may include a sleeve 1812, tentacles 1814, frame 1816, second sleeve 1836, second frame 1846, tubular hub 1876, and middle sleeve portion 1878. The sleeve 1812 may extend from a first end 1818 to a second end 1820. The sleeve 1812 may have an interior 1822 that extends to an opening 1824 at the first end 1818. The frame 1816 may extend between a first end 1830 and a second end 1832. The second sleeve 1836 may extend from first end 1840 to second end 1842. The second frame 1846 may extend between a first end 1848 and a second end 1850. The occlusion device 1810 may be similar in all respects to the occlusion device 1610 of FIG. 21, except that the occlusion device 1710 may lack the second tentacles 1638, and that the second sleeve may have a closed rounded first end 1840 rather than a circular open end. The closed rounded first end 1840 may be attached to the exterior or interior of the second frame 1846 to facilitate occlusion when blood flows through the opening 1824 of the sleeve 1812.

FIG. 24 illustrates an occlusion device 1910 in accordance with some embodiments of the present disclosure. The occlusion device 1910 may include a sleeve 1912, tentacles 1914, frame 1916, tubular hub 1976, and middle sleeve portion 1978. The sleeve 1912 may extend from a first end 1918 to a second end 1920 and may have an interior 1922 that may extend to an opening 1924. The frame 1916 may extend between a first end 1930 and a second end 1932. The occlusion device 1810 may be similar in the occlusion devices previously described. That sleeve 1912 may be similar to the second sleeve 1836 of FIG. 23. For example, the sleeve 1912 may have a closed rounded first end 1918 which may be attached to the exterior or interior of the frame 1916. The tentacles 1914 may extend from the inflection points (or substantially from the inflection points) of the longitudinal members in a direction longitudinally toward the hub 1976.

FIGS. 25 and 26 depict a delivery assembly 2000 for introducing and retrieving any of the occlusion devices (designated in FIG. 26 with reference numeral 2014) of FIGS. 1-24 for occluding a body vessel in accordance with some embodiments of the present disclosure. However, one skilled in the art will recognize that other delivery assemblies may be used for introducing and retrieving the occlusion device 2014. As shown, the delivery assembly 2000 includes a polytetrafluoroethylene (PTFE) introducer sheath 2002 for percutaneously introducing an outer sheath 2004 into a body vessel. Of course, any other suitable material for the introducer sheath 2002 may be used without falling beyond the scope or spirit of the present invention. The introducer sheath 2002 may have any suitable size. The introducer sheath 2002 serves to allow the outer sheath 2004 and an inner member or catheter 2006 to be percutaneously inserted to a desired location in the body tissue, cavity or vessel. The inner member may also include, for example, a stylet. The introducer sheath 2002 receives the outer sheath 2004 and provides stability to the outer sheath 2004 at a desired location of the body tissue, cavity or vessel. For example, the introducer sheath 2002 is held stationary within the body tissue, cavity or vessel, and adds stability to the outer sheath 2004, as the outer sheath 2004 is advanced through the introducer sheath 2002 into an opening. The outer sheath 2004 has a body extending from a proximal end 2016 to a distal end 2010, the body being tubular and including a sheath lumen extending therethrough.

As shown, the assembly 2000 may also include a wire guide 2008 configured to be percutaneously inserted within the vasculature to guide the outer sheath 2004 to the opening. The wire guide 2008 provides the outer sheath 2004 with a path to follow as it is advanced within the body tissue, cavity or vessel. The size of the wire guide 2008 is based on the inside diameter of the outer sheath 2004 and the diameter of the target opening.

When the distal end 2010 of the outer sheath 2004 is at the desired location within the opening, the wire guide 2008 is removed and the occlusion device 2014, which may contact a distal portion 2012 of the inner catheter 206, is inserted into the outer sheath 2004. The inner catheter 2006 is advanced (e.g. pushed) through the outer sheath 2004 for deployment of the occlusion device 2014 through the distal end 2010 to occlude the opening. The catheter 2006 extends from a proximal portion 2011 to a distal portion 2012 and is configured for longitudinal movement relative to the outer sheath 2004. In this example, the distal portion 2012 is shown adjacent to the occlusion device 2014 before introduction into the outer sheath 2004. Thus, before deployment, the occlusion device 2014 is coaxially disposed within the lumen of the outer sheath 2004 and removably coupled (e.g. by a hook of the occlusion device 2014) to the distal portion 2012 of the catheter 2006, or in the alternative, the occlusion device 2014 is merely pushed by, but not coupled to, the distal portion 2012 of the catheter 2006.

The outer sheath 2004 further has a proximal end 2016 and a hub 2018 to receive the inner catheter 2006 and occlusion device 2014 to be advanced therethrough. The size of the outer sheath 2004 is based on the size of the body tissue, cavity vessel in which it percutaneously inserts, the size of the opening, and/or the size of the occlusion device 2014.

In this embodiment, the occlusion device 2014 and inner catheter 2006 are coaxially advanced through the outer sheath 2004, following removal of the wire guide 208, in order to position the occlusion device 2014 to occlude the body vessel. The occlusion device 2014 is guided through the outer sheath 2004 by the inner catheter 2006, preferably from the hub 2018, and exits from the distal end 2010 of the outer sheath 2004 at a location within the opening. Thus, the occlusion device 2014 is deployable through the distal end 2010 of the outer sheath 2004 by means of longitudinal relative movement of the catheter 2006. In order to more easily deploy the occlusion device 2014 into the body vessel, the occlusion device 2014 may have a slippery coating, such as Silicone or slipcoating. If the occlusion device 2014 is self-expanding, the occlusion device 2014 may self-expand from the radially collapsed state to the radially expanded state in response to, for example, temperature changes (e.g. if the occlusion device 2014 is made of Nitinol), or for example, because the occlusion device 2014 will return to its biased radially expanded state after being compressed in the outer sheath 2004 in its radially collapsed state.

Likewise, this embodiment may also retrieve the occlusion device 2014 by positioning the distal end 2010 of the outer sheath 2004 adjacent the deployed device in the vasculature. The inner catheter 2006 is advanced through the outer sheath 2004 until the distal portion 2012 protrudes from the distal end 2010 of the outer sheath 2004. The distal portion 2012 (e.g. which may include a snare) is coupled to a proximal end of the occlusion device 2014 (e.g. to a retrieval member such as a hook or loop), after which the inner catheter 2006 is retracted proximally, drawing the occlusion device 2014 into the outer sheath 2004.

Figure 27:
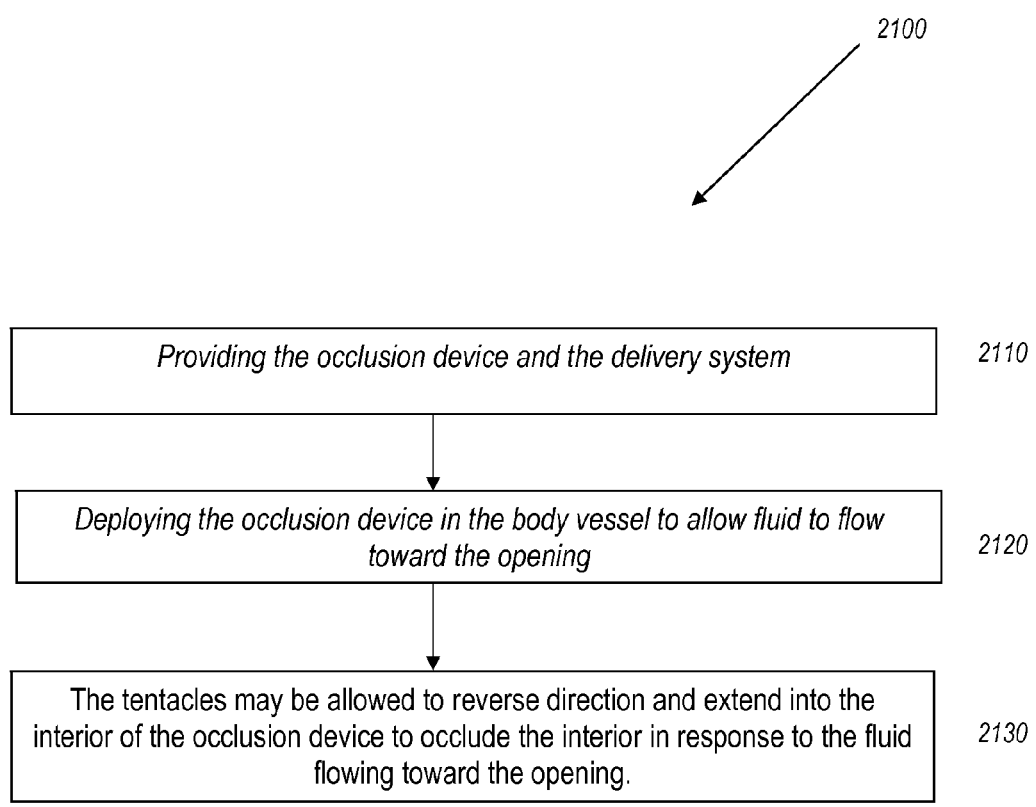
FIG. 27 is a flowchart depicting a method for occluding a body vessel with an occlusion device and a delivery apparatus in accordance with some embodiments of the present disclosure.

FIG. 27 illustrates a method 2100 for occluding a body vessel with any of the occlusion devices of FIGS. 1-24 and with the delivery apparatus of FIGS. 25 and 26 in accordance with some embodiments of the present disclosure. The ordering of the steps presented herein is merely one implementation of the method 2100. Those skilled in the art will recognize that the ordering may be varied, that some steps may occur simultaneously, that some steps may be omitted, and that further steps may be added. In block 2110, any of the occlusion devices of FIGS. 1-24 and the delivery system of FIG. 2526 may be provided. The method may proceed from block 2110 to block 2120. In block 2120, the occlusion device may be deployed in the body vessel to allow fluid to flow toward the opening. In occlusion devices having two sets of tentacles (e.g. attached to opposing sleeve openings), the occlusion device may be deployed in any of the two orientations allowing fluid to flow toward an opening. The method may proceed from block 2120 to block 2130. In block 2130, the plurality of tentacles may be allowed to reverse direction and extend into the interior to occlude the interior in response to the fluid flowing toward the opening.

As a person skilled in the art will readily appreciate, the above description is meant as an illustration of implementation of the principles of this invention. This description is not intended to limit the scope or application of this invention in that the invention is susceptible to modification, variation and change, without departing from the spirit of this invention, as defined in the following claims.

What is claimed is:

1. An occlusion device for occluding a body vessel, the occlusion device comprising:
   a sleeve extending from a first end to a second end and defining a longitudinal axis therebetween, the sleeve having an interior that extends to an opening at the first end, wherein the second end is closed;
   a plurality of tentacles having a first end attached to the first end of the sleeve and extending longitudinally away from the second end of the sleeve, the plurality of tentacles being flexible and configured to reverse direction and extend longitudinally toward the second end of the sleeve and into the interior of the sleeve to occlude the interior of the sleeve in response to fluid flowing toward the opening and from the first end to the second end of the sleeve; and
   a frame having a first end and second end and defining a longitudinal axis therebetween and an interior, wherein the frame is attached to the first end of the sleeve and the sleeve is located in the interior of the frame.

2. The occlusion device of claim 1 wherein the sleeve comprises a plurality of woven fibers.

3. The occlusion device of claim 1 wherein the sleeve comprises a plurality of molded fibers.

4. The occlusion device of claim 1 wherein the sleeve has a conical shape.

5. The occlusion device of claim 1 wherein the second end of the sleeve comprises a rounded end.

6. The occlusion device of claim 1 further comprising:
   a second sleeve extending from a first end to a second end, the second sleeve having a second interior that extends to a second opening at the first end, wherein the first end is attached to the frame; and
   a second plurality of tentacles attached to the first end and extending away from the sleeve, the plurality of tentacles configured to reverse direction and extend into the second interior to occlude the second interior in response to fluid flowing toward the second opening.

7. The occlusion device of claim 6 wherein the second end of the sleeve is attached to the second end of the second sleeve.

8. The occlusion device of claim 1 further comprising a retrieval member attached to the frame.

9. The occlusion device of claim 1 wherein the frame has a tubular shape.

10. The occlusion device of claim 1 wherein the frame has a conical shape.

11. The occlusion device of claim 1 further comprising hooks attached to the frame to prevent migration of the occlusion device.

12. The occlusion device of claim 1, wherein the second end of the sleeve is located longitudinally between the first and second ends of the frame.

13. A method of occluding a body vessel with an occlusion device, the occlusion device comprising a sleeve extending from a first end to a second end and defining a longitudinal axis therebetween, the sleeve having an interior that extends to an opening at the first end, wherein the second end is closed, the occlusion device further comprising a plurality of tentacles having a first end attached to the first end of the sleeve and extending longitudinally away from the sleeve second end of the, the plurality of tentacles being flexible, the occlusion device further comprising a frame having a first end and second end and defining a longitudinal axis therebetween and an interior, wherein the frame is attached to the first end of the sleeve and the sleeve is located in the interior of the frame, the method comprising:
    deploying the occlusion device in the body vessel to allow fluid to flow toward the opening; and
    allowing the plurality of tentacles to reverse direction and extend longitudinally toward the second end of the sleeve and into the interior of the sleeve to occlude the interior in response to the fluid flowing toward the opening and from the first end to the second end of the sleeve.

14. The method of claim 13 wherein the sleeve comprises a plurality of woven fibers.

15. The method of claim 13 wherein the sleeve comprises a plurality of molded fibers.

16. The method of claim 13 wherein the sleeve has a conical shape.

17. The method of claim 13 wherein the second end of the sleeve comprises a rounded end.

18. The method of claim 13 further comprising retrieving the occlusion device from the body vessel by grasping a retrieval member that is attached to the frame.

19. The method of claim 13 wherein the frame has a tubular shape.

20. The method of claim 13 wherein the frame has a conical shape.

21. The method of claim 13 preventing migration of the occlusion device by allowing hooks attached to the frame to engage the body vessel.

22. A delivery assembly for placing and retrieving an occlusion device for occluding an opening in a body tissue, the assembly comprising:
    an outer sheath having a tubular body extending from a proximal part to a distal part and the tubular body including a sheath lumen extending therethrough;
    an inner member extending from a proximal portion to a distal portion, the inner member being disposed within the sheath lumen and configured for longitudinal movement relative to the outer sheath;
    the occlusion device being coaxially disposed within the sheath lumen and removably coupled to the distal portion of the inner member and deployable through the distal part of the outer sheath by means of the relative longitudinal movement of the inner member, the occlusion device comprising:
        a sleeve extending from a first end to a second end and defining a longitudinal axis therebetween, the sleeve having an interior that extends to an opening at the first end, wherein the second end is closed;
        a plurality of tentacles having a first end attached to the first end of the sleeve and extending longitudinally away from the second end of the sleeve, the plurality of tentacles being flexible and configured to reverse direction and extend longitudinally toward the second end of the sleeve and into the interior of the sleeve to occlude the interior of the sleeve in response to fluid flowing toward the opening and from the first end to the second end of the sleeve; and
        a frame having a first end and second end and defining a longitudinal axis therebetween and an interior, wherein the frame is attached to the first end of the sleeve and the sleeve is located in the interior of the frame.

* * * * *